United States Patent
Sasaki et al.

(10) Patent No.: US 9,120,724 B2
(45) Date of Patent: Sep. 1, 2015

(54) METHOD FOR PRODUCING ABSOLUTE ALCOHOL AND ABSOLUTE ALCOHOL

(75) Inventors: Hideo Sasaki, Chiba (JP); Mitsuhiro Hamano, Kyoto (JP); Masato Uchiki, Kyoto (JP)

(73) Assignee: TAKARA SHUZO CO., LTD., Kyoto (JP)

( * ) Notice: Subject to any disclaimer, the term of this patent is extended or adjusted under 35 U.S.C. 154(b) by 0 days.

(21) Appl. No.: 14/241,996

(22) PCT Filed: Sep. 7, 2012

(86) PCT No.: PCT/JP2012/072927
§ 371 (c)(1),
(2), (4) Date: Feb. 28, 2014

(87) PCT Pub. No.: WO2013/035849
PCT Pub. Date: Mar. 14, 2013

(65) Prior Publication Data
US 2014/0213830 A1    Jul. 31, 2014

(30) Foreign Application Priority Data
Sep. 9, 2011  (JP) .................................. 2011-197560

(51) Int. Cl.
*C07C 31/08* (2006.01)
*B01D 61/36* (2006.01)
*B01D 71/02* (2006.01)
*C07C 29/76* (2006.01)

(52) U.S. Cl.
CPC .............. *C07C 31/08* (2013.01); *B01D 61/362* (2013.01); *B01D 71/028* (2013.01); *C07C 29/76* (2013.01)

(58) Field of Classification Search
None
See application file for complete search history.

(56) References Cited

U.S. PATENT DOCUMENTS

| 4,395,576 A | 7/1983 | Kwantes et al. |
| 4,448,644 A | 5/1984 | Foster et al. |

FOREIGN PATENT DOCUMENTS

| JP | 57-28016 | 2/1982 |
| JP | 57-145822 | 9/1982 |
| JP | 58-021629 | 2/1983 |
| JP | 61-074568 | 4/1986 |
| JP | 04-193304 | 7/1992 |
| JP | 10-147546 | 6/1998 |
| JP | 2002-345495 | 12/2002 |
| JP | 2006-083129 | 3/2006 |
| JP | 2006-263561 | 10/2006 |
| JP | 2006-263561 A | * 10/2006 | ............... B01D 3/36 |
| JP | 2008-086972 | 4/2008 |
| JP | 2009-066519 | 4/2009 |
| JP | 2011-105601 | 6/2011 |
| WO | 2009/107840 | 9/2009 |
| WO | 2009/123222 | 10/2009 |
| WO | 2009/123223 | 10/2009 |

OTHER PUBLICATIONS

Database CAPLUS on STN, Acc. No. 2008:960915, Sato et al., Microporous and Mesoporous Materials (2008), 115(1-2), pp. 184-188 (abstract).*
Database CAPLUS on STN, Acc. No. 2007:1023936, Aoki et al., Maku (2007), 32(4), pp. 234-237 (abstract).*
Database CAPLUS on STN, Acc. No. 2003:207982, Ichikawa et al., Preprints of Symposia-American Chemical Society, Division of Fuel Chemistry (2003), 48(1), pp. 492-493 (abstract).*
International Preliminary Report on Patentability issued Mar. 12, 2014 in corresponding Application No. PCT/JP2012/072927.
"Jozo no Jiten" (Encyclopedia of brewing), Nov. 10, 1988, Asakura Publishing Co., Ltd., (1st Ed.) pp. 366-369.
International Search Report issued Nov. 27, 2012 in International (PCT) Application No. PCT/JP2012/072927.
Zeolite Membrane Element, "*Hitz Dehydration System HDS*", Hitachi Zosen Corporation, online, Retrieved from the Internet: URL: http://www.hitachizosen.co.jp/english/products/products009.html (cited in communication from JPO on May 8, 2015.

* cited by examiner

*Primary Examiner* — Brian J Davis
(74) *Attorney, Agent, or Firm* — Wenderoth, Lind & Ponack, L.L.P.

(57) ABSTRACT

A method for producing an absolute alcohol containing not more than 0.4 mg/L of acetal by subjecting a raw material alcohol to a zeolite membrane treatment, the raw material alcohol being obtained by distilling a crude alcohol, and having an alcohol concentration of not less than 95 v/v%, and the raw material alcohol containing not more than 5 mg/L of acetaldehyde and not more than 60 mg/L of a total amount of organic impurities. An absolute alcohol can be produced, which absolute alcohol is highly safe to the human body and has a quality that no off-odor is felt by human senses. In addition, the contents of diacetyl and crotonaldehyde in the raw material alcohol may be set at levels not more than particular values, respectively.

17 Claims, No Drawings

METHOD FOR PRODUCING ABSOLUTE ALCOHOL AND ABSOLUTE ALCOHOL

TECHNICAL FIELD

The present invention relates to a method for producing an absolute alcohol and to an absolute alcohol. In more detail, the present invention relates to a method for producing an absolute alcohol with an acetal content of not more than a predetermined value using a crude alcohol as a raw material, and to an absolute alcohol. The absolute alcohol of the present invention is of high safety and high quality free from off-odor.

BACKGROUND ART

Ethanol (alcohol) is widely used in industries not only for beverages as alcoholic drinks but also for chemical industry, food industry and pharmaceutical products. Ethanol for alcoholic drinks and food additives is called as a brewed alcohol or a fermented alcohol and produced from natural raw materials such as molasses, sweet potatoes, and cereals by fermentation.

Industrial alcohols other than brewed alcohols are produced from ethylene as a raw material by chemical synthesis, thus called as synthetic alcohols. Almost all of ethanol other than the brewed alcohol and pharmaceutical alcohol is called as a denatured alcohol that contains an added substance such as methanol or isopropyl alcohol. A denatured alcohol used for external preparations or cosmetics is made to be unsuitable for drink by adding isopropyl alcohol which is less toxic than methanol or by giving bitterness or odor, although it does not contain methanol as a denaturant.

Recently, in Japan, a brewed alcohol is produced by a method for producing highly pure ethanol containing negligible impurities by purifying an imported alcohol with a highly advanced Japanese distillation mode, which imported alcohol is obtained overseas by distilling fermented mash from a natural raw material using a relatively simple distiller (referred to a "crude alcohol"). As an example of the highly advanced distillation mode, a distiller of super allospase mode is used (Non-Patent Document 1). In this mode, most of impurities such as low-boiling impurities such as aldehyde and methanol, and middle- and high-boiling impurities containing fusel oil components such as 1-propanol are separated using a number of columns such as a fermented mash column (A column), a separation column (A1 column), a concentration column (A2 column), an extraction column (D column), a rectifying column (B column), a purification column (C column), an impurities treatment column (G column), and a reduced pressure column (H column). Particularly, in the D column, hot water is injected from the top of the column to keep the ethanol concentration within the column at approximately 10 w/w %, thereby changing the relative volatility between ethanol and the other low-boiling and middle- to high-boiling impurities to effectively separate those impurities at the top of the column. However, it is known that the crude alcohol contains ethanol with a concentration of 90% by mass or more, but also contains a trace of other impurities that cannot be separated by the super allospase mode.

In the category of ethanol (alcohol), there is "absolute ethanol" (absolute alcohol) that contains 99.5 v/v % or more of ethanol at 15° C. General methods for producing an absolute alcohol include azeotropic distillation. That is, hydrous ethanol is azeotropically distilled with ethyl acetate or benzene to attain an ethanol content of 99.5 v/v %. It is difficult, however, to avoid mixing of a trace of ethyl acetate or benzene in the absolute alcohol obtained by azeotropic distillation. Accordingly, it is not preferable in some cases to adopt absolute ethanol produced by azeotropic distillation as a raw material for a substance that directly contacts with a human body such as an external preparation or a cosmetic.

As an alternative technique to the azeotropic distillation, a technique for producing an absolute alcohol by membrane separation has been developed. For example, a method for producing an absolute alcohol by combining distillation and membrane separation is known (for example, Patent Documents 1 and 2).

Patent Document 1 proposes a separation apparatus including a distillation means and a membrane separation means having a zeolite membrane for separating mixed vapor which distills off from the column top of the distillation means. This document describes converting an ethanol/water liquid mixture to vapor having an ethanol concentration of 91.0% by mass (equivalent to about 94 v/v %) by the distillation means, and then purifying the vapor till the ethanol concentration reaches 99.5% by mass (equivalent to 99.69 v/v %) through the zeolite membrane.

Patent Document 2 also discloses a separation apparatus of almost the same concept as in Patent Document 1. This apparatus improves the separation performance by being equipped with a plurality of separation membrane modules.

Further, a purification treatment method for obtaining an absolute alcohol from a fermented aqueous alcohol solution by a membrane separation technique is known (Patent Documents 3-5). It is considered that according to this technique, 99.8% by mass (equivalent to 99.88 v/v %) of absolute ethanol can be obtained with good energy efficiency by the purification treatment of a fermented aqueous ethanol solution with an ethanol concentration of 7.3% by mass (equivalent to about 9 v/v %). In this technique, however, only separation of impurities through two columns of fermented mash column and distillation column is performed because importance is given to energy efficiency, and the ethanol concentration in the distillation column is at most 85-90% by mass (equivalent to about 90-93.5 v/v %).

Thus, there is no problem such as mixing of a trace of ethyl acetate and benzene as in azeotropic distillation in the combination of distillation and membrane separation as described in Patent Documents 1-5. In addition, an absolute alcohol obtained by the combination of distillation and membrane separation is being put to practical use as bioethanol fuel to be used instead of petroleum.

PATENT DOCUMENTS

Patent Document 1: JP 2006-263561A
Patent Document 2: JP 2009-66519A
Patent Document 3: WO 2009/107840
Patent Document 4: WO 2009/123222
Patent Document 5: WO 2009/123223

NON-PATENT DOCUMENT

Non-Patent Document 1: "Jozo no Jiten" (Encyclopedia of brewing), Nov. 10, 1988, Asakura Publishing Co., Ltd., (1$^{st}$ Ed.), pp. 366-367

DISCLOSURE OF INVENTION

Technical Problem

As described above, it is preferable that ethanol used as a raw material for external preparations and cosmetics does not contain ethyl acetate and benzene from the viewpoint of safety. In addition, ethanol is strongly required to be free of off-odor. Besides, Patent Documents 1-5 do not refer to off-odor of the obtained absolute alcohol at all.

Thus, an object of the present invention is to provide a highly safe absolute alcohol of high quality free from off-odor, and a method for producing the same.

Means for Solving the Problem

The present inventors noticed the frequent formation of ethanol with off-odor in the course of studying the production technique of absolute ethanol by membrane separation. Therefore, the inventors attempted to identify the cause of off-odor generation. As a result, the inventors found that acetal is one of substances causing off-odor. Further, the inventors found that the formation of acetal is predominantly attributable to acetaldehyde existing in the raw material before membrane separation, and further that the presence of organic impurities such as diacetyl and crotonaldehyde in a certain amount of more in the raw material before membrane separation also greatly influences on the quality of the absolute alcohol. Then, the inventors found that an absolute alcohol without off-odor that can be felt by human senses, namely free from off-odor can be produced by a membrane treatment of a raw material alcohol containing a small amount of acetaldehyde and total organic impurities and having an alcohol concentration of not less than 95 v/v %, and completed the present invention. The present invention provided to solve the above-described problem is as follows.

An aspect of the present invention is a method for producing an absolute alcohol containing not more than 0.4 mg/L of acetal by subjecting a raw material alcohol to a zeolite membrane treatment, the raw material alcohol being obtained by distilling a crude alcohol, and having an alcohol concentration of not less than 95 v/v %, and the raw material alcohol containing not more than 5 mg/L of acetaldehyde and not more than 60 mg/L of a total amount of organic impurities.

In the method for producing an absolute alcohol of this aspect, a raw material alcohol obtained by distillation of a crude alcohol is subjected to a zeolite membrane treatment. In this aspect, an absolute alcohol containing not more than 0.4 mg/L of acetal is obtained by using the raw material alcohol having an alcohol concentration of not less than 95 v/v %, and containing not more than 5 mg/L of acetaldehyde and not more than 60 mg/L of a total amount of organic impurities. According to this aspect, it is possible to produce a highly safe absolute alcohol having a quality that no off-odor is felt by human senses.

The term "alcohol concentration" refers to the concentration of ethyl alcohol (ethanol). That is, the term "alcohol" herein refers to, unless otherwise indicated, ethyl alcohol (ethanol).

The term "absolute alcohol" refers to ethanol containing not less than 99.5 v/v % of ethanol at 15° C.

The term "crude alcohol" refers to an alcohol obtained by distilling fermented mash from a natural raw material using a relatively simple distiller.

The term "organic impurities" refers to the whole organic compounds other than ethanol. Typically, the organic impurities include twelve kinds of main components, namely, methyl alcohol, isopropyl alcohol, acetaldehyde, n-propyl alcohol, n-butyl alcohol, 2-butyl alcohol, isobutyl alcohol, active amyl alcohol, acetone, 1,4-dioxane, diacetyl, and crotonaldehyde. Further typically, the organic impurities consist of the twelve kinds of organic compounds.

The term "total amount of organic impurities" means the sum of the organic impurity content.

The term "acetal" means acetaldehyde diethyl acetal $((CH_3CH_2O)_2CHCH_3)$.

Preferably, the organic impurities consist of methyl alcohol, isopropyl alcohol, acetaldehyde, n-propyl alcohol, n-butyl alcohol, 2-butyl alcohol, isobutyl alcohol, active amyl alcohol, acetone, 1,4-dioxane, diacetyl, and crotonaldehyde. That is, it is preferable that the sum of the contents of these twelve kinds of organic impurities is not more than 60 mg/L.

Preferably, the raw material alcohol contains not more than 0.03 mg/L of diacetyl and not more than 0.3 mg/L of crotonaldehyde.

This preferable aspect focuses on diacetyl and crotonaldehyde in addition to acetaldehyde as the organic impurities.

Preferably, the raw material alcohol contains not more than 0.01 mg/L of diacetyl and not more than 0.2 mg/L of crotonaldehyde.

Preferably, the raw material alcohol contains not more than 3 mg/L of acetaldehyde, 0.01-0.03 mg/L of diacetyl, and not more than 0.2 mg/L of crotonaldehyde.

Preferably, the raw material alcohol contains not more than 2 mg/L of acetaldehyde, not more than 0.01 mg/L of diacetyl, and 0.2-0.3 mg/L of crotonaldehyde.

Preferably, the raw material alcohol contains not more than 1 mg/L of acetaldehyde, 0.01-0.03 mg/L of diacetyl, and 0.2-0.3 mg/L of crotonaldehyde.

Preferably, the treatment includes contacting a gas mixture with the zeolite membrane, and the gas mixture is obtained by heating the raw material alcohol Preferably, the organic impurities consist of methyl alcohol, isopropyl alcohol, acetaldehyde, n-propyl alcohol, n-butyl alcohol, 2-butyl alcohol, isobutyl alcohol, active amyl alcohol, acetone, 1,4-dioxane, diacetyl, and crotonaldehyde, the raw material alcohol contains not more than 0.03 mg/L of diacetyl and not more than 0.3 mg/L of crotonaldehyde, the treatment includes contacting a gas mixture with the zeolite membrane, and the gas mixture is obtained by heating the raw material alcohol.

Another aspect of the present invention is an absolute alcohol produced from a crude alcohol as a raw material, wherein the absolute alcohol contains not more than 0.4 mg/L of acetal.

The absolute alcohol of this aspect is produced from a crude alcohol as a raw material, wherein the acetal content is not more than a particular amount. The absolute alcohol of this aspect is highly safe, and has a quality that no off-odor is felt by human senses. The absolute alcohol of the present invention is suitable for a raw material for external preparations and cosmetics.

Still another aspect of the present invention is an absolute alcohol obtainable by the above-described method for producing an absolute alcohol, wherein the absolute alcohol contains not more than 0.4 mg/L of acetal.

The absolute alcohol of this aspect is obtainable by the above-described method of the present invention for producing an absolute alcohol. The absolute alcohol of this aspect is highly safe, and has a quality that no off-odor is felt by human senses. The absolute alcohol of this aspect is suitable for a raw material for external preparations and cosmetics.

Advantageous Effect of Invention

According to the method of the present invention for producing an absolute alcohol, it is possible to obtain a highly safe absolute alcohol free from off-odor felt by human senses, that is, free from off-odor.

The absolute alcohol of the present invention is highly safe and has no off-odor. Hence, the absolute alcohol is suitable for a raw material for external preparations and cosmetics.

DESCRIPTION OF EMBODIMENT

In the following, embodiments of the present invention will be specifically described.

The method of the present invention for producing an absolute alcohol is a method for producing an absolute alcohol containing not more than 0.4 mg/L of acetal by subjecting a raw material alcohol to a zeolite membrane treatment, the raw material alcohol being obtained by distilling a crude alcohol, and having an alcohol concentration of not less than 95 v/v %, and the raw material alcohol containing not more than 5 mg/L of acetaldehyde and not more than 60 mg/L of a total amount of organic impurities.

In the present invention, the raw material alcohol subjected to a zeolite membrane treatment contains not more than 5 mg/L of acetaldehyde and not more than 60 mg/L of a total amount of organic impurities. Thereby, when the subsequent zeolite membrane treatment is performed, an absolute alcohol free from off-odor that can be felt by human senses, in other words, free from off-odor can be obtained. In this specification, the unified term "free from off-odor" is used to refer to the fact that no off-odor is felt by human senses.

As described above, the term "crude alcohol" used in the present invention is an alcohol obtained by distilling fermented mash originated from a natural raw material using a relatively simple distiller.

As described above, the term "organic impurities" used in the present invention refers to the whole organic compounds other than ethanol. Typically, the organic impurities include twelve kinds of main components, namely, methyl alcohol, isopropyl alcohol, acetaldehyde, n-propyl alcohol, n-butyl alcohol, 2-butyl alcohol, isobutyl alcohol, active amyl alcohol, acetone, 1,4-dioxane, diacetyl, and crotonaldehyde. Further typically, the organic impurities consist of the twelve kinds of organic compounds. That is, in preferable embodiments, the sum of contents of the twelve kinds of organic impurities is not more than 60 mg/L.

In the present invention, the sum of whole organic impurities contained in the raw material alcohol is not more than 60 mg/L, more preferably not more than 55 mg/L, further preferably not more than 50 mg/L.

In the present invention, the content of acetaldehyde in the raw material alcohol is not more than 5 mg/L, more preferably not more than 3 mg/L, further preferably not more than 2 mg/L, particularly preferably not more than 1 mg/L.

Some substances other than acetal that is assumed to predominantly ascribable to acetaldehyde also influence on the quality (off-odor) of the absolute alcohol. For example, diacetyl and crotonaldehyde, which are organic impurities, contained in a particular amount in the raw material alcohol affect the quality of the absolute alcohol. Hence, it is preferable in the present invention that the diacetyl content is not more than 0.03 mg/L and the crotonaldehyde content is not more than 0.3 mg/L in the raw material alcohol. It is further preferable that the diacetyl content is not more than 0.01 mg/L and the crotonaldehyde content is not more than 0.2 mg/L in the raw material alcohol.

Further, it is preferable that the acetaldehyde content is not more than 3 mg/L, the diacetyl content is 0.01-0.03 mg/L, and the crotonaldehyde content is not more than 0.2 mg/L in the raw material alcohol. In addition, it is preferable that the acetaldehyde content is not more than 2 mg/L, the diacetyl content is not more than 0.01 mg/L, and the crotonaldehyde content is 0.2-0.3 mg/L in the raw material alcohol. Further, it is preferable that the acetaldehyde content is not more than 1 mg/L, the diacetyl content is 0.01-0.03 mg/L, and the crotonaldehyde content is 0.2-0.3 mg/L in the raw material alcohol.

The method for distilling a crude alcohol is not particularly restricted, and any distillation method may be used as long as highly pure raw material ethanol can be obtained. However, in order to perform distillation in an industrial scale, for example, the above-described super allospase mode is the most suitable. Distillation of a crude alcohol gives a raw material alcohol having an alcohol concentration of not less than 95 v/v %, an acetaldehyde content of not more than 5 mg/L, and a whole organic impurity content of not more than 60 mg/L. Then, this raw material alcohol is subjected to a zeolite membrane treatment. Considering energy efficiency in distillation, it is preferable that the alcohol concentration of the obtained raw material alcohol is in the range of 95-97 v/v %.

Examples of the separation means utilizing a membrane separation method include a pervaporation method (PV method) in which a particular liquid is separated by making a liquid mixture contact with one side (supplying side) of the separation membrane and reducing the pressure of the opposite side (permeating side) of the membrane, as well as a vapor permeation method (VP method) in which particular vapor is separated by supplying a gas mixture in the state of vapor to make the mixture contact with a separation membrane, and reducing the pressure of the permeating side. In the present invention, although either of the PV method and the VP method can be adopted, the VP method is preferable in which a raw material alcohol as a gas mixture is contacted with a zeolite membrane. In the case of adopting the VP method, for example, a raw material alcohol is heated to 110-130° C., more preferably 110-120° C., to generate a gas mixture. Then, the gas mixture is subjected to a zeolite membrane treatment.

As described above, the "zeolite membrane treatment" herein means performing a separation treatment of a liquid mixture or a gas mixture using a zeolite membrane.

The type of the zeolite membrane may be selected as appropriate, depending upon the properties of the substance to be selectively permeated. In the case of selective separation of water from an ethanol/water vapor mixture as an example of a separation treatment of a gas mixture, that is, mixed vapor, the membrane may be selected from zeolite membranes having selective water permeability such as a type A zeolite membrane, a type Y zeolite membrane, a type NaX zeolite membrane, a type T zeolite membrane, mordenite of low Si/Al ratio and a ZSM-5 type zeolite membrane of low Si/Al ratio. Among them, a type A zeolite membrane with high selective water permeability, especially an NaA type zeolite membrane is preferably used.

Further, a zeolite membrane module with a zeolite membrane housed therein may be used. For example, a large membrane area is obtained by using a zeolite membrane module in which two or more NaA type zeolite membranes are housed. When a large amount of raw material alcohol is to be subjected to the zeolite membrane treatment, these zeolite membrane modules maybe set in parallel.

The extent of pressure reduction at the secondary side (permeating side) of the membrane in the zeolite membrane treatment maybe nearly vacuum. For example, the treatment may be performed at a pressure of not more than 10 Torr relative to 760 Torr of the atmospheric pressure, in other words, at a pressure of not more than −750 mmHg relative to the atmospheric pressure.

Next, the method for producing an absolute alcohol of the present invention will be further explained.

The method for obtaining a raw material alcohol with an alcohol concentration of not less than 95 v/v % by distillation of a crude alcohol will be illustrated. The method for producing a raw material alcohol with an alcohol concentration of 95 v/v % can be performed, without any particular restriction, based on the production method of a raw material alcohol of high purity containing extremely little impurities using a distiller of super allospase mode. Fundamentally, a fermented mash column (A column), a rectifying column (B column), and a purification column (C column) are used, and in the case where a large amount of organic impurities are contained in the crude alcohol, columns such as an extraction column (D column) and a reduced pressure column (H column) may be used as appropriate.

In the case where a large amount of organic impurities such as crotonaldehyde are contained, the organic impurity content may be reduced, for example, by a method described in JP 2002-345495A. When a large amount of 1,4-dioxane is contained as organic impurities, 1,4-dioxane may be reduced, for example, by a method described in JP 2006-83129A.

An absolute alcohol with an alcohol concentration of 99.9 v/v % is produced by distilling a crude alcohol to give a raw material alcohol with an alcohol concentration of not less than 95 v/v %, having an acetaldehyde content of 5 mg/L and a whole organic impurity content of not more than 60 mg/L, preferably not more than 55 mg/L, more preferably not more than 50 mg/L, and then using a zeolite membrane module. The obtained absolute alcohol has an acetal content of not more than 0.4 mg/L and is of high quality free of off-odor.

It has been confirmed that an absolute alcohol with an alcohol concentration of 99.9 v/v % can be obtained according to the method of the present invention.

The absolute alcohol of the present invention is produced using a crude alcohol as a raw material, and contains not more than 0.4 mg/L of acetal. If the acetal content is more than 0.4 mg/L, the absolute alcohol has off-odor which can be felt by human senses. Among external preparations and cosmetics, for example, a hairdressing contains an absolute alcohol as its component, and contacts directly with the human body. Thus, unless the absolute alcohol is off-odor free, the commercial value of the product will be lost. Accordingly, a high-quality hairdressing can be obtained by using an absolute alcohol with an acetal content of not more than 0.4 mg/L free from off-odor. In addition, it has been confirmed that components such as inorganic substances constituting the zeolite membrane do not elute.

The present invention also encompasses an absolute alcohol containing not more than 0.4 mg/L of acetal, that is obtained by subjecting a raw material alcohol to a zeolite membrane treatment, the raw material alcohol being obtained by distilling a crude alcohol, and having an alcohol concentration of not less than 95 v/v %, and the raw material alcohol containing not more than 5 mg/L of acetaldehyde and not more than 60 mg/L of a total amount of organic impurities.

EXAMPLES

In the following, the present invention will be explained with reference to examples in more detail, but the present invention is not limited to these examples.

Example 1

A raw material alcohol with an ethanol concentration of 95.5 v/v % was obtained by distilling a crude alcohol with an ethanol concentration of 95.0 v/v % using a continuous distiller of super allospase mode. The components of the raw material alcohol were analyzed by GC/MS in which a mass selection type detector was connected to gas chromatograph in the usual manner. As a result, the raw material alcohol contained 1.0 mg/L of acetaldehyde, 0.01 mg/L of diacetyl, 0.1 mg/L of crotonaldehyde, and 38 mg/L of other organic impurities (organic impurities other than acetaldehyde, diacetyl, and crotonaldehyde).

The obtained raw material alcohol was heated to make a gas mixture, which was subjected to a zeolite membrane treatment by a VP method to yield an absolute alcohol with an ethanol concentration of 99.9 v/v %. The used zeolite membrane module housed eight sheets of NaA type zeolite membranes and had a membrane area of 2400 $cm^2$. The components of the absolute alcohol were analyzed by GC/MS in the usual manner. As a result, the absolute alcohol contained 1.0 mg/L of acetaldehyde, 0.01 mg/L of diacetyl, 0.1 mg/L of crotonaldehyde and 40 mg/L of other organic impurities. Acetal was not detected (detection limit: 0.01 mg/L).

The raw material alcohol and absolute alcohol obtained in Example 1 were subjected to a sensory test for the existence of off-odor and the like by eleven skilled panelists. As a result, in either of the raw material alcohol and the absolute alcohol, eleven out of the eleven panelists responded that they did not feel off-odor at all and the alcohols are of high quality.

Comparative Example 1

Acetaldehyde was added to the crude alcohol with an ethanol concentration of 95.0 v/v % used in Example 1 to prepare a sample of a crude alcohol with an acetaldehyde content of 6.0 mg/L. This sample was distilled using a continuous distiller of super allospase mode to give a raw material alcohol with an ethanol concentration of 95.5 v/v %. Acetaldehyde was again added to the obtained raw material alcohol to prepare an alcohol sample with an acetaldehyde content of 6.0 mg/L. This sample was treated with a zeolite membrane in the same manner as in Example 1 to give an absolute alcohol with an ethanol concentration of 99.9 v/v %. This absolute alcohol contained 6.1 mg/L of acetaldehyde, 0.01 mg/L of diacetyl, 0.1 mg/L of crotonaldehyde, and 40 mg/L of other organic impurities. The acetal content was 0.5 mg/L.

The raw material alcohol and absolute alcohol obtained in Comparative Examples 1 were subjected to a sensory test for the existence of off-odor and the like by eleven skilled panelists. As a result, for the raw material alcohol, eleven out of the eleven panelists responded that they did not feel off-odor at all and the alcohols are of high quality. On the other hand, for the absolute alcohol, eleven out of the eleven panelists responded that they felt off-odor.

Comparative Example 2

A crude alcohol with an ethanol concentration of 95.0 v/v % of a different lot from that in Example 1 was used. This crude alcohol contained a large amount of crotonaldehyde. To this crude alcohol, acetaldehyde and diacetyl were added to prepare a sample of a crude alcohol containing a large amount of crotonaldehyde, 6.0 mg/L of aldehyde, and 0.04 mg/L of diacetyl. This sample was distilled using a continuous distiller of super allospase mode to give a raw material alcohol with an ethanol concentration of 95.5 v/v %. To the obtained raw material alcohol, acetaldehyde was again added to prepare an alcohol sample with an acetaldehyde content of 6.0 mg/L. This sample was treated with a zeolite membrane in the same manner as in Example 1 to give an absolute alcohol with an ethanol concentration of 99.9 v/v %. This absolute alcohol contained 6.1 mg/L of acetaldehyde, 0.04 mg/L of diacetyl, 0.2 mg/L of crotonaldehyde, and 46 mg/L of other organic impurities. The content of acetal was 0.5 mg/L.

The raw material alcohol and absolute alcohol obtained in Comparative Examples 2 were subjected to a sensory test for the existence of off-odor and the like by eleven skilled panelists. As a result, for the raw material alcohol, eleven out of the eleven panelists responded that they felt off-odor a little. For the absolute alcohol, eleven out of the eleven panelists responded that they felt off-odor.

The invention claimed is:

1. A method for producing an absolute alcohol containing not more than 0.4 mg/L of acetal by subjecting a raw material alcohol to a zeolite membrane treatment,
   the raw material alcohol being obtained by distilling a crude alcohol, and having an alcohol concentration of not less than 95 v/v %, and
   the raw material alcohol containing not more than 5 mg/L of acetaldehyde and not more than 60 mg/L of a total amount of organic impurities.

2. The method according to claim 1, wherein the organic impurities consist of methyl alcohol, isopropyl alcohol, acetaldehyde, n-propyl alcohol, n-butyl alcohol, 2-butyl alcohol, isobutyl alcohol, active amyl alcohol, acetone, 1,4-dioxane, diacetyl, and crotonaldehyde.

3. The method according to claim 1, wherein the raw material alcohol contains not more than 0.03 mg/L of diacetyl and not more than 0.3 mg/L of crotonaldehyde.

4. The method according to claim 2, wherein the raw material alcohol contains not more than 0.03 mg/L of diacetyl and not more than 0.3 mg/L of crotonaldehyde.

5. The method according to claim 3, wherein the raw material alcohol contains not more than 0.01 mg/L of diacetyl and not more than 0.2 mg/L of crotonaldehyde.

6. The method according to claim 4, wherein the raw material alcohol contains not more than 0.01 mg/L of diacetyl and not more than 0.2 mg/L of crotonaldehyde.

7. The method according to claim 3, wherein the raw material alcohol contains not more than 3 mg/L of acetaldehyde, 0.01-0.03 mg/L of diacetyl, and not more than 0.2 mg/L of crotonaldehyde.

8. The method according to claim 4, wherein the raw material alcohol contains not more than 3 mg/L of acetaldehyde, 0.01-0.03 mg/L of diacetyl, and not more than 0.2 mg/L of crotonaldehyde.

9. The method according to claim 3, wherein the raw material alcohol contains not more than 2 mg/L of acetaldehyde, not more than 0.01 mg/L of diacetyl, and 0.2-0.3 mg/L of crotonaldehyde.

10. The method according to claim 4, wherein the raw material alcohol contains not more than 2 mg/L of acetaldehyde, not more than 0.01 mg/L of diacetyl, and 0.2-0.3 mg/L of crotonaldehyde.

11. The method according to claim 3, wherein the raw material alcohol contains not more than 1 mg/L of acetaldehyde, 0.01-0.03 mg/L of diacetyl, and 0.2-0.3 mg/L of crotonaldehyde.

12. The method according to claim 4, wherein the raw material alcohol contains not more than 1 mg/L of acetaldehyde, 0.01-0.03 mg/L of diacetyl, and 0.2-0.3 mg/L of crotonaldehyde.

13. The method according to claim 1, wherein
    the treatment comprises contacting a gas mixture with the zeolite membrane, and
    the gas mixture is obtained by heating the raw material alcohol.

14. The method according to claim 2, wherein
    the treatment comprises contacting a gas mixture with the zeolite membrane, and
    the gas mixture is obtained by heating the raw material alcohol.

15. The method according to claim 3, wherein
    the treatment comprises contacting a gas mixture with the zeolite membrane, and
    the gas mixture is obtained by heating the raw material alcohol.

16. The method according to claim 4, wherein
    the treatment comprises contacting a gas mixture with the zeolite membrane, and
    the gas mixture is obtained by heating the raw material alcohol.

17. The method according to claim 1, wherein the absolute ethanol is free from off-odor.

* * * * *